(12) United States Patent
Braunecker et al.

(10) Patent No.: US 8,379,191 B2
(45) Date of Patent: Feb. 19, 2013

(54) SCANNER SYSTEM AND METHOD FOR REGISTERING SURFACES

(75) Inventors: Bernhard Braunecker, Rebstein (CH); Peter Stegmaier, Ponte Capriasca (CH); Peter Kipfer, Marbach (CH)

(73) Assignee: Leica Geosystems AG, Heerbrugg (CH)

( * ) Notice: Subject to any disclaimer, the term of this patent is extended or adjusted under 35 U.S.C. 154(b) by 1004 days.

(21) Appl. No.: 11/610,650

(22) PCT Filed: Jun. 21, 2005

(86) PCT No.: PCT/EP2005/052880
§ 371 (c)(1),
(2), (4) Date: Feb. 1, 2010

(87) PCT Pub. No.: WO2006/000552
PCT Pub. Date: Jan. 5, 2006

(65) Prior Publication Data
US 2011/0032507 A1 Feb. 10, 2011

(30) Foreign Application Priority Data
Jun. 23, 2004 (EP) .................................... 04014704

(51) Int. Cl.
*G01C 3/08* (2006.01)
(52) U.S. Cl. .................. 356/4.07; 356/4.01; 356/4.1
(58) Field of Classification Search ............. 356/4.07, 356/5.01, 451, 600–608
See application file for complete search history.

(56) References Cited

U.S. PATENT DOCUMENTS

| 4,627,734 A | 12/1986 | Rioux |
| 4,645,347 A | 2/1987 | Rioux |
| 4,800,271 A | 1/1989 | Blais |
| 5,018,854 A | 5/1991 | Rioux |
| 5,075,561 A | 12/1991 | Rioux |
| 5,177,556 A | 1/1993 | Rioux |
| 5,296,702 A | 3/1994 | Beck et al. |
| 5,701,173 A | 12/1997 | Rioux |
| 5,708,498 A | 1/1998 | Rioux et al. |
| 5,837,997 A | 11/1998 | Beck et al. |
| 5,946,645 A | 8/1999 | Rioux et al. |
| 6,009,359 A | 12/1999 | El-Hakim et al. |

(Continued)

FOREIGN PATENT DOCUMENTS

| CA | 1332633 | 10/2004 |
| EP | 1 480 006 | 11/2004 |

(Continued)

OTHER PUBLICATIONS

High-Speed Noncontact Profiler Based on Scanning White-light Interferometry, Lesile Deck, Peter deGroot, Applied Optics, vol. 33, No. 31, Nov. 1, 1994.*

(Continued)

*Primary Examiner* — Luke Ratcliffe
(74) *Attorney, Agent, or Firm* — Maschoff Gilmore & Israelsen

(57) ABSTRACT

The invention relates to a method for registering surfaces, using a scanner system comprising a radiation source for emitting electromagnetic radiation (ES), a scanning device for guiding the radiation over the surface in order to scan the latter and a receiver for receiving the radiation (RS) that is reflected by the surface. According to the invention, the radiation is spectrally separated to analyze the surface characteristics and a distance measuring unit is used to derive distance information in parallel from the received radiation.

24 Claims, 7 Drawing Sheets

U.S. PATENT DOCUMENTS

| | | | |
|---|---|---|---|
| 6,043,506 A * | 3/2000 | Heffelfinger et al. | 250/584 |
| 6,271,918 B2 | 8/2001 | Blais | |
| 6,297,488 B1 | 10/2001 | Beraldin | |
| 6,330,523 B1 * | 12/2001 | Kacyra et al. | 702/159 |
| 6,507,036 B1 | 1/2003 | Godin | |
| 6,806,953 B2 * | 10/2004 | Hoffmann et al. | 356/317 |
| 7,012,615 B2 | 3/2006 | Kraemer | |
| 7,202,776 B2 * | 4/2007 | Breed | 340/435 |
| RE41,175 E * | 3/2010 | Vashisth et al. | 342/357.31 |
| 7,916,278 B2 * | 3/2011 | Smith | 356/4.01 |
| 2004/0232317 A1 | 11/2004 | Ura et al. | |
| 2008/0319321 A1 * | 12/2008 | Goldbach | 600/475 |

FOREIGN PATENT DOCUMENTS

| | | |
|---|---|---|
| WO | 9740342 | 10/1997 |
| WO | 03031910 | 4/2003 |
| WO | 04036145 | 12/2006 |

OTHER PUBLICATIONS

Deck, Lesie, DeGroot Pater, High-Speed Noncontact Profiler Based on the Scanning White-Light Interferometer. Applied Optics. vol. 33, No. 21, Nov. 1994.*

Seigen Peter, Terahertz Technology, IEEE Transactions on Microwave Theory and Techniques, vol. 50, No. 3, Mar. 2002.*

* cited by examiner

SCANNER SYSTEM AND METHOD FOR REGISTERING SURFACES

The invention relates to a scanner system for registering surfaces according to the preamble of claim 1, a method for registering surfaces according to the preamble of claim 15 and a geodetic device and a mobile scanning system.

Methods which successively scan and record the topography of a structure, such as, for example, a construction, are frequently used for registering surfaces. Such a topography represents a cohesive sequence of points which describe the surface or a corresponding model or a description of the surface. A customary approach is scanning by means of a laser scanner which in each case registers the spatial position of a surface point by measuring the distance to the targeted surface point by the laser and linking this measurement to the angle information of the laser emission. From this distance and angle information, the spatial position of the registered point can be determined and the surface continuously surveyed. In many cases, image recording by a camera, which also provides further information, for example with regard to the surface texture, in addition to the overall visual view, is also carried out simultaneously with this purely geometrical registration of the surface.

Thus, for example, WO 97/40342 describes a ground-based method which records a topography by scanner systems directed in a fixed position. For these systems, a fixed erection point which serves as a basis of a. scanner process carried out by means of motors is chosen. The three-dimensional location information of the respective surface point can be derived from the distance to the measured point, the angle position at the time of the measurement and the known location of the scanning device. Scanner systems are designed especially for the object of registering topography and scan a surface by movement of the scanner system or by changing the beam path.

In addition, scanning functions can be integrated into various other devices as additional functions. WO 2004/036145 discloses, for example, a geodetic measuring device which emits a laser beam for distance measurement from its position within the registered range. Such measuring devices can also be modified for registering surfaces by scanning or can be operated without modification. Motorized theodolites or total stations represent an example of this.

Other methods use mobile systems which scan a structure to be registered by a movement of the scanner system or support or supplement the scanning. Such systems are particularly suitable for registering linear structures or structures which can be driven on in a linear manner, such as, for example, track installations, roads, tunnel systems or airfields.

Such registration processes of the prior art provide images or topographical data which substantially represent the information about spatial distribution or relative arrangement of surface points. Optionally, additionally recorded images permit the derivation of further information.

Consequently, the structure and the contour of the surface can be comparatively readily reconstructed. However, the lack of qualitative data on the type and characteristics of the surface, in particular with regard to the internal structure or composition, is disadvantageous. Thus, images recorded parallel to the scanning generally permit the identification of different brightness values. Although these can be interpreted with regard to possible structures and compositions of the surface and the underlying processes, further information must be provided for this purpose or greatly limiting assumptions must be made.

Thus, for example, in the case of recordings of tunnel systems in the images produced in parallel, it is possible to recognize dark spots which can be interpreted as water spots. The same applies to the recognition of colored layers or top layers which separate off and which significantly change the reflection behavior of the surface. A precondition of these greatly simplified interpretations is of course a limitation of the latitude of interpretation, which is based on prior information—in this case the knowledge of water outflows or spot formations.

A recording, in parallel with the registration of the surface, of a parameter which permits an analytical characterization of the surface over and above a simple consideration of grey step values cannot be performed by methods of the prior art.

An object of the present invention is to provide a scanner system and a method which permits at least a qualitative analysis of a surface in parallel to the registration of the surface.

A further object is to check or verify qualitative parameters of the surfaces.

A further object is the provision of a system which permits a higher functionality than the pure registration of surfaces, for example by permitting a warning function in the case of a qualitative change of registered structures.

The invention relates to a scanner system and a method for registering a surface and a geodetic measuring device equipped with the system or a mobile scanning system.

According to the invention, the surface is spectrally probed in parallel with scanning, i.e. is scanned so that conclusions can be drawn about the composition or the state of the probed or registered surface from the spectral components of the radiation received. The spectral probing can be effected for the entire surface topography, in particular continuously, or for partial areas. In principle, a separate spectral emission or a spectral analysis can be effected after or during reception of the radiation. Likewise, the two approaches can be combined.

For the spectrally separated or separate emission, for example, radiation can be emitted in two spectral ranges separated from one another or two partly overlapping spectral ranges, synchronously or in an alternating manner. In conventional scanner systems of the prior art, it is sufficient for this purpose, in addition to the laser radiation source already used for scanning and distance measurement, to integrate a second laser whose emission is guided over the same beam path so that the surface is scanned in an identical manner. The emitted radiation thereof may be on the long-wave but also the short-wave side of the laser conventionally used for the distance measurement, the short-wave option also being capable of permitting, for example, fluorescence measurements. In parallel or additionally, multispectral or white light sources can also be used.

The reception can be effected, for example, with only one receiver if, in the case of alternating emission, this receives the reflection in the different spectral ranges as a function of time. In the case of simultaneous emission, for example, it is possible to use two spectrally selective receivers, from the relative intensities of which conclusions can be drawn about the material giving rise to the reflection. For example, a system can be designed for detecting rust on concrete surfaces and can emit two complementary radiations in the red and blue range. Red, rust-containing surface regions will have increased reflection in the red spectral range compared with only moist or dry concrete sections, so that, in contrast to the pure light-dark evaluation, rust can be distinguished from wet areas by this method. Such a simple method or scanner system can be used for identifying previously known patterns, as occur, for example, in the monitoring of constructions.

Scanner systems and methods which offer higher spectral resolution and hence more comprehensive potential uses permit an extended field of use. According to the invention, spectrometers are used for this purpose in order to spectrally resolve or to analyze the radiation received. According to the invention, in principle all types of spectrometers, such as, for example, prism, grating, terahertz or Fourier transform spectrometers, can be used. However, most surface-scanning systems permit only a short time span for analysis since the alignment of the beam path with a point to be registered and to be surveyed is very short. Spectrometers which require a comparatively long duration for analysis can be used only if disadvantages are accepted, such as, for example, greater structural complexity due to the use of a plurality of spectrometers overlapping as a function of time in operation, or reduced scanning speed.

Spectrometers which are sufficiently fast with respect to the scanning speed or effect a spatial demodulation can therefore advantageously be used. Fourier spectrometers based on the Michelson principle, which have an inclined mirror so that a path difference results not by adjustment of the mirror but depending on location, constitute an example of the last-mentioned spectrometers. The resulting interference pattern is recorded by a suitable arrangement, such as, for example, a photodiode array or a CCD/CMOS camera, and subsequently subjected to a transformation or spectral resolution. Sufficiently fast transformations for harmonic decomposition are available for this purpose, even for the scanning process, such as, for example, the discrete Fourier transformation (DFT).

Suitable designs and methods of production for miniaturized Fourier spectrometers are described in the thesis "Micro-sized Fourier Spectrometers" by Omar Manzardo, University of Neuchatel, Switzerland, Jan. 2002.

According to the invention, the spectral separation can therefore be effected by a spectrally selective emission, by a spectral analysis after or during reception or by a combination of the two approaches, the chosen solution also being dependent on the type of surface to be detected or analyzed and the composition thereof.

A further possibility is probing by means of terahertz sources, which permit both a certain depth of penetration and hence an analysis down to below the surface of materials or topographies thereof as well as an improved analysis in special areas. Suitable terahertz technologies have long been realized, for example, for the astronomical area, more compact systems suitable in principle for a scanner application now also being available. Sources used may be, for example, mode-coupled titanium:sapphire lasers with photoconductive dipole antenna, femtosecond lasers with electrooptical crystals and electronic Gunn/Bloch oscillators, which, together with a reflective optical system, permit a more compact arrangement. On the receiver side, it is possible to realize compact terahertz spectrometers, for example, based on Hilbert Transform spectrometers.

A scanner system according to the invention and a method according to the invention are described in more detail below purely by way of example with reference to working examples shown schematically in the drawing.

Specifically,

Figure 1:
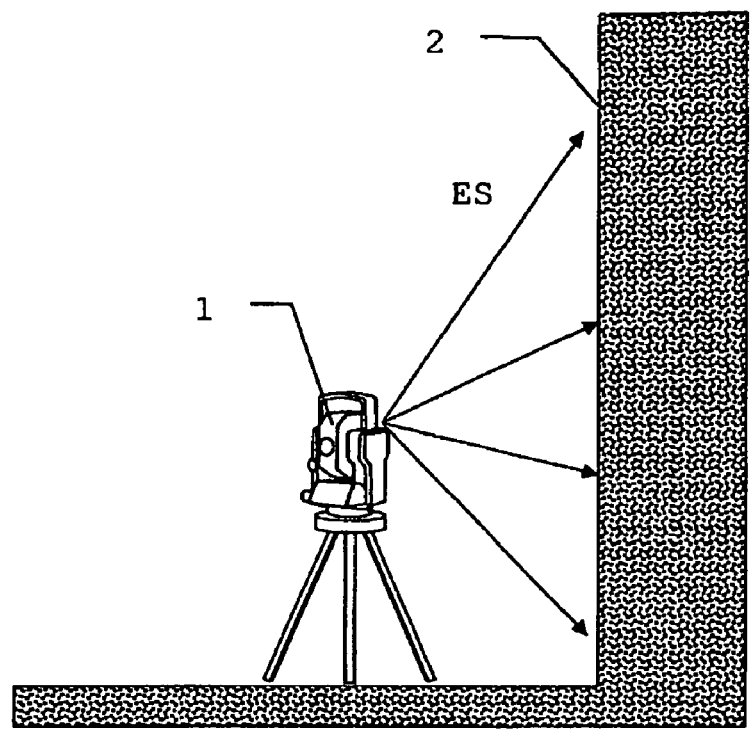
FIG. 1 shows the scanning of an outer surface by means of a geodetic device of the prior art.

FIG. 1 explains by way of example the scanning of an outer surface 2 by means of a geodetic device 1 of the prior art. The geodetic device 1 is positioned a sufficient distance away from the outer surface 2 and scans the outer surface 2 at different angle positions, electromagnetic radiation ES being emitted for distance measurement. The outer surface 2 can be reconstructed from the distance measurements and the coordinated angle positions. The desired resolution of the surface registration determines the subdivision of the registered region into angle positions. Parallel to the distance measurements, it is also possible to record images by a camera in the geodetic device.

Figure 2:
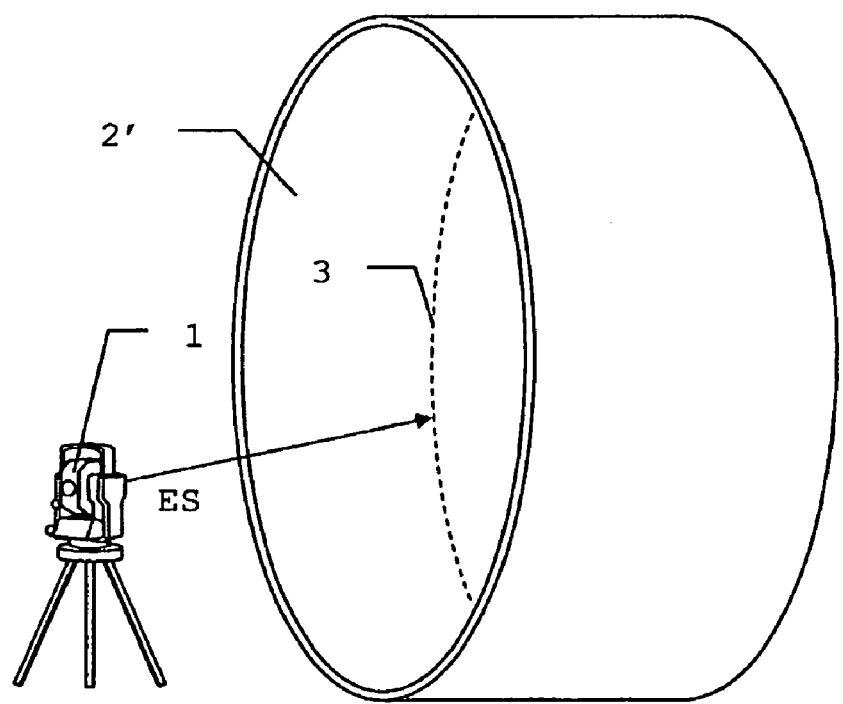
FIG. 2 shows the schematic diagram of a method of the prior art for scanning the inner surface of a tunnel by means of a geodetic device of the prior art.

FIG. 2 shows the schematic diagram of a method of the prior art for scanning the inner surface 2' of a structure by means of a geodetic device 1 of the prior art. In a manner similar to the procedure from example 1, it is also possible to scan inner surfaces 2' of structures, such as, for example, tunnels, underpasses or interior rooms of buildings, by means of geodetic devices 1. By means of the electromagnetic radiation ES, the inside 2' is scanned in the form of a spiral track 3 and thus registered. Owing to the narrower registration area at greater depths of the structure, the geodetic device 1 generally has to be used with frequent changes in position, for example upside down.

Figure 3:
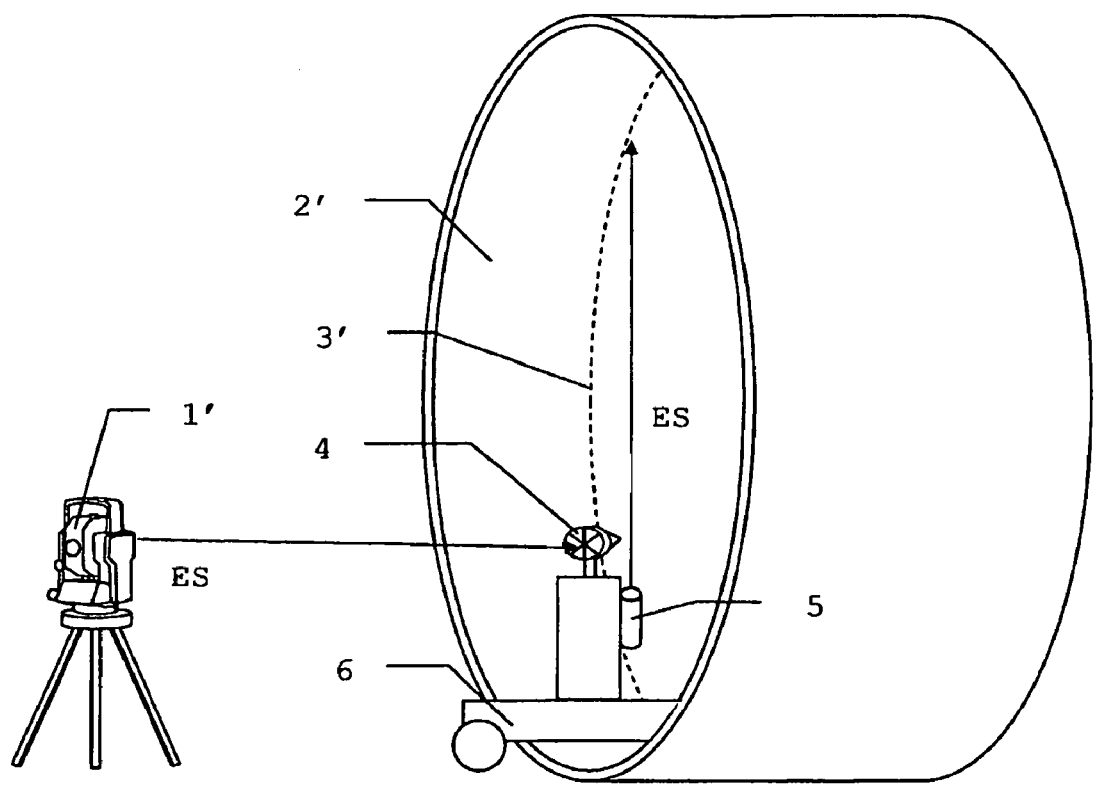
FIG. 3 shows the schematic diagram of a method according to the invention for scanning the inner surface of a tunnel by means of a mobile scanning system according to the invention.

In comparison, FIG. 3 shows the schematic diagram of a method according to the invention for scanning the inner surface 2' of the same tunnel by means of a mobile scanning system 6 according to the invention. Inside the tunnel, the mobile scanning system 6 is moved in a linear manner, the inner surface 2' being scanned by electromagnetic radiation ES continuously along a spiral or zigzag track 3'. The emission direction is continuously varied by pivoting the transmitting and receiving unit 5, the position of the mobile scanning system 6 being determined by a fixed geodetic device 1', such as, for example, a motorized theodolite with automatic target tracking, which continuously measures angle and distance to a retroreflector 4 mounted on the mobile scanning system 6. The radiation reflected by the inner surface 2' is registered by the transmitting and receiving unit 5 and spectrally analyzed so that, in addition to the topographic contour of the surface, it is also possible to derive further information.

Figure 4:
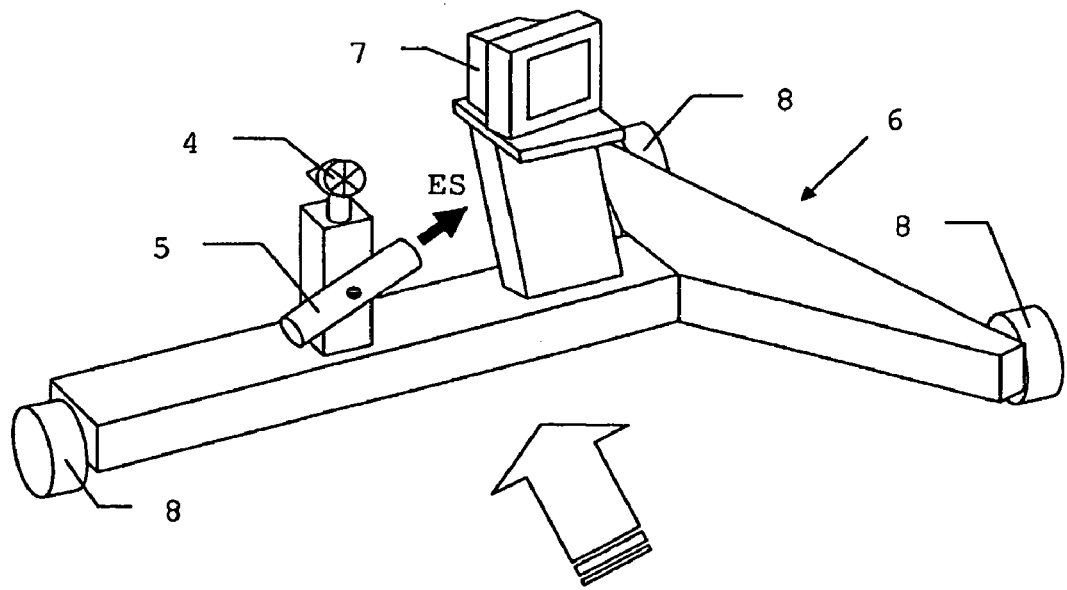
FIG. 4 shows the schematic diagram of a mobile scanning system according to the invention.

FIG. 4 shows the schematic diagram of a mobile scanning system according to the invention. The mobile scanning system 6 is based on a carriage-like body which is mobile by means of rollers 8. The transmitting and receiving unit 5 pivotable through about 180° and the retroreflector 4 together with a computing and control unit 7 are arranged on the body. The pivotable transmitting and receiving unit 5 moves at a speed which is chosen so that both a distance measurement and the spectral analysis can be carried out for each angle position and longitudinal position of the transmitting and receiving unit 5. Here, the electromagnetic radiation ES is emitted and received via the transmitting and receiving unit 5, it being possible to arrange radiation source and sensor both in the pivotable transmitting and receiving unit 5 itself or at another point, such as, for example, in the body of the mobile scanning system 6. By means of a mobile scanning system 6 according to the invention, it is possible to register and analyze, rapidly and in a continuous process, accessible structures, in particular linear ones, with regard to form and composition of their surface, inner surfaces 2' also having the advantage of a small scattered light component.

Figure 5:
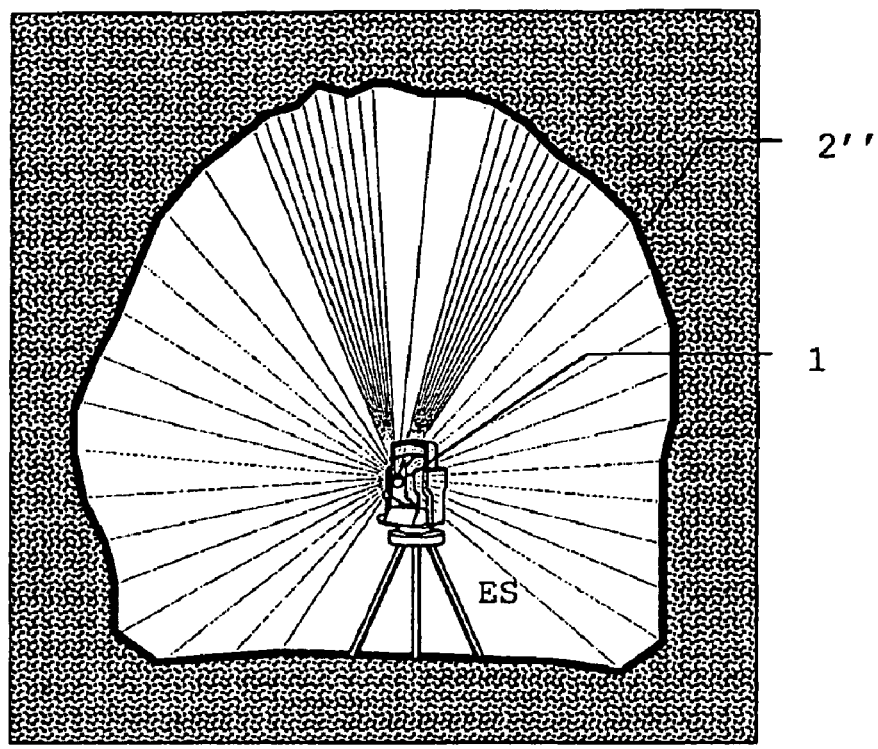
FIG. 5 shows the scanning of the inner surface of a structure in cross-section by means of a geodetic device of the prior art.

FIG. 5 explains the scanning of the inner surface 2" of a structure in cross-section by means of a geodetic device 1 of the prior art. Scanning of the form of the inner surface 2" of a structure, which is shown here by way of example as an unlined tunnel, is effected by the electromagnetic radiation ES of the geodetic device 1. The registration does not permit any conclusions about structures and changes present below the inner surface 2" or structures of the surfaces below the resolution of the distance measurement. If a camera for image recording is used in parallel, the range of analysis is extended but in particular no analysis of the chemical composition or of the spectral reflectivity of the inner surface 2" can be effected.

Figure 6:
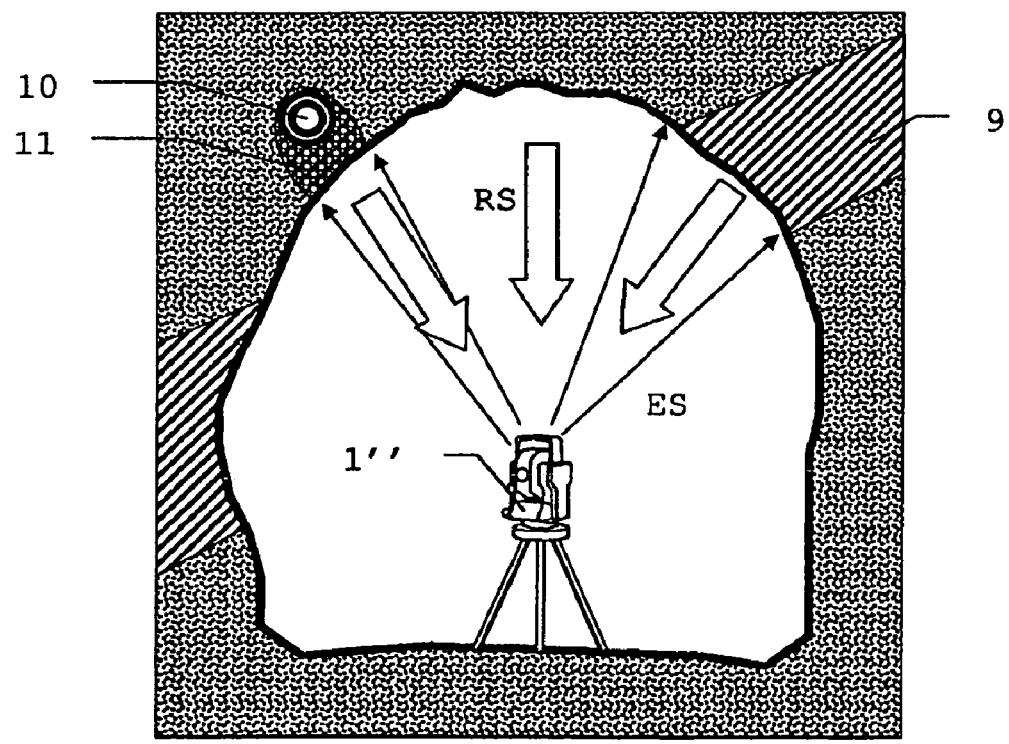
FIG. 6 shows the scanning of the inner surface of a structure by means of a geodetic device according to the invention.

In comparison, a geodetic device 1" according to the invention permits the scanning of the inner surface of the same structure with an extended possibility of analysis, as shown schematically in FIG. 6. The electromagnetic radiation ES emitted by the geodetic device 1 is sent back by the surface as reflected radiation RS with spectral information and is received again by the geodetic device 1". Depending on the composition of the surface, there is a change in the spectrum of the reflected radiation RS compared with the emission. Thus, on the basis of the spectral distribution or of the harmonic components, it is also possible to identify structures below the surface. In this example, the position and extent of a water-carrying stratum 9 can be recognized from the wetting of the surface visible in the tunnel. Likewise, liquid emerging from a pipe 10 can be recognized. In a similar manner, however, rust on reinforcement steel meshes embedded in reinforced concrete can be recognized and localized. In combination with marking substances which have particular spectral susceptibility, it is possible according to the invention also to carry out a search for leaks by loading the pipe to be investigated with the marking substance and localizing the point of emergence by means of a scanner system.

Figure 7:
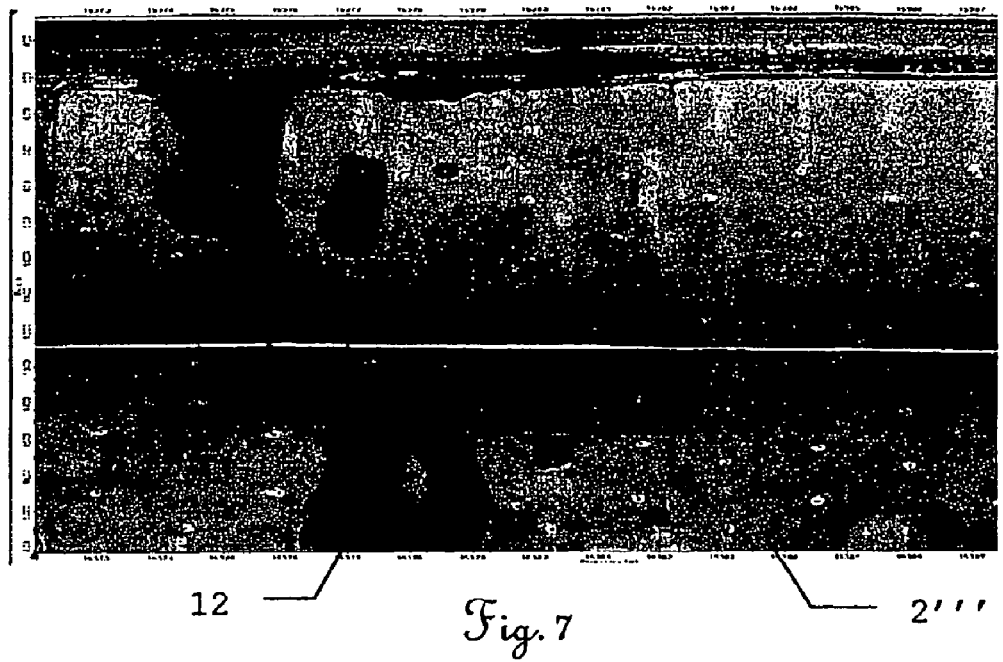
FIG. 7 shows an example of a gray step recording of the inside of a tunnel with identifiable structures.

FIG. 7 shows an example of a grey step recording of the inner surface 2''' of a tunnel with identifiable structures. The image corresponds to a recording of a region close to the bottom of the tunnel to the tunnel ceiling with a registration range of almost 180°. The continuous white line in the lower image half represents the high voltage wire of an overhead line. Dark spots 12 in the grey step recording can be interpreted, for example, as moist areas. However, they may alternatively also be an area of peeling surface deposit, so that an analysis over and above the grey step representation is advantageous.

The embodiments of the scanner system according to the invention or of a geodetic device according to the invention, shown in the following FIGS. 8-13, are explained in abstract terms with reference to their substantial components. Details of beam guidance, such as, for example, elements of transmitting and receiving optical system, are not shown for reasons of clarity. Likewise, there is no detailed presentation of scanner components used for beam guidance or for compensating effects or artifacts produced by the scanning process. The individual working examples are only exemplary possibilities of the realizations with the use of interchangeable components. In particular, the elements and their arrangement can be combined with one another in the various FIGS. 8-13.

Figure 8:
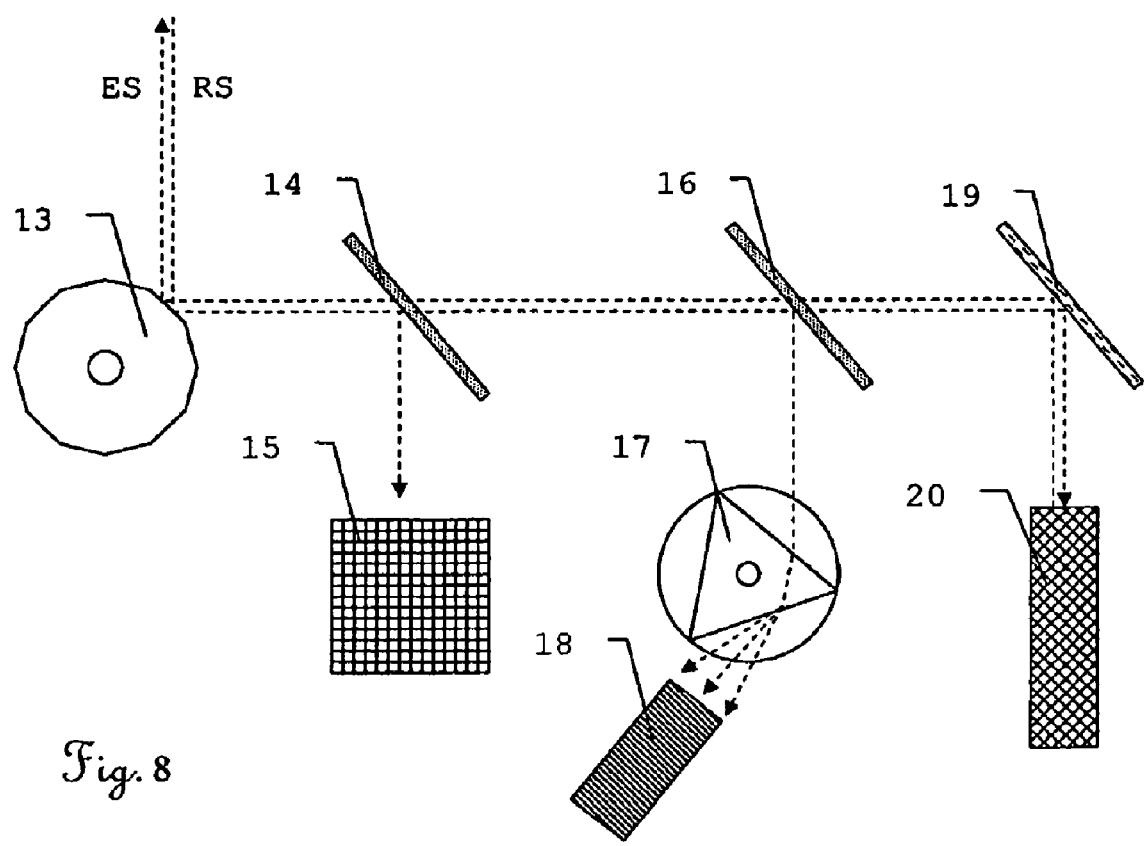
FIG. 8 shows the schematic diagram of a first working example of a scanner system according to the invention.

FIG. 8 shows the schematic diagram of a first working example with a rotating prism spectrometer 17. A laser diode as a radiation source, arranged in a distance-measuring device 20, emits electromagnetic radiation ES via a deflection mirror 19 and a scanner wheel 13 onto the surface to be scanned. Here, the scanner wheel 13 shown is typical for a scanning device known per se from the prior art. After reflection by the surface to be registered, the radiation is received again as reflected radiation RS and guided via the scanner wheel and the deflection mirror 19 back to a distance measuring device which is arranged in the distance-measuring device 20 and which derives distance information from the reflected radiation RS, in particular by the pulse transit time or phase measuring method.

A first beam splitter 16 which guides a part of the reflected radiation RS on to the prism spectrometer 17 is present in this beam path. Said spectrometer has, for example, a rotatable equilateral prism or a star-like arrangement of prisms or prism surfaces. By rotation of the prism, the geometric conditions are continuously changed and the spectral components are passed in succession on to a downstream detector 18 so that the latter registers a spectrum of the reflected radiation RS and evaluates it in downstream electronics. Here, scanner wheel 13 and prism spectrometer 17 must be synchronized in their rotation so that a spectral analysis by the prism spectrometer can be effected for each surface point to be registered. A second beam splitter 14 outputs a further part of the reflected radiation RS, which is guided onto a camera 15, for example a CCD or CMOS camera chip, for image acquisition and processing.

Figure 9:
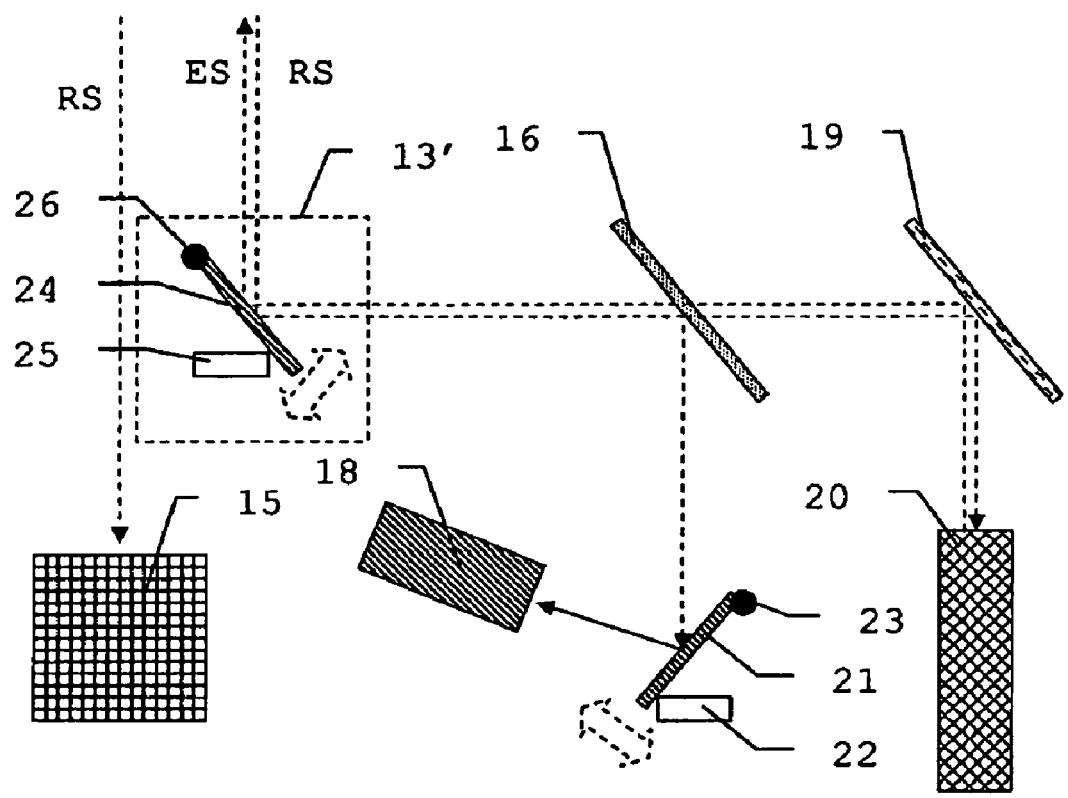
FIG. 9 shows the schematic diagram of a second working example of a scanner system according to the invention.

FIG. 9 shows the schematic diagram of a second working example comprising a grating spectrometer. A radiation source arranged in a distance-measuring device 20 emits electromagnetic radiation ES onto the surface to be scanned via a deflection mirror 19 and a mirror surface 24 pivotable by means of a piezo element 25 about an axis 26, as scanning device 13'. The mirror surface 24 pivotable for scanning and shown here is typical for a further scanning device known from the prior art. After reflection by the surface to be registered, the radiation is received again as reflected radiation RS and guided via the pivotable mirror surface 24 and the deflection mirror 19 back onto a distance-measuring device arranged in the distance-measuring device 20. A first beam splitter 16 outputs light from the beam path onto the grating spectrometer. Said spectrometer has a grating 21 which is pivotable about an axis 23 and is operated in this working example—in particular as a blazed grating—in reflection. A piezo element 22 is used as an adjusting device. By movement of the pivotable grating 21, the extremes of the various orders are projected in succession onto a detector 18 so that a spectral analysis can be carried out. A beam path for a camera 15 is formed parallel to the axis of the receiving device for the spectrometer and the distance measuring device. Depending on sensitivity and intended use, the camera 15 can use the light of the radiation source of the distance-measuring device, a separate light source, e.g. an LED, or daylight for recording. According to the invention, it is also possible to use other types of grating spectrometers, for example a lamellar grating interferometer or a grating on a curved and adjustable mirror.

Figure 10:
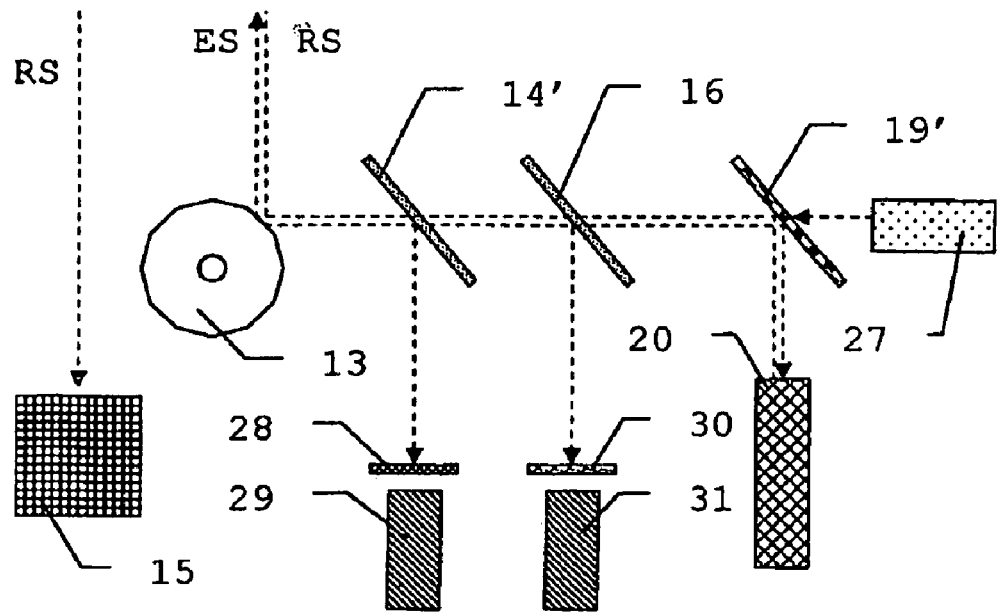
FIG. 10 shows the schematic diagram of a third working example of a scanner system according to the invention.

FIG. 10 explains a third working example of a scanner system according to the invention on the basis of a schematic diagram. A radiation source arranged in a distance-measuring device 20 emits electromagnetic radiation ES via a dichroic deflection mirror 19' and a scanner wheel 13 on to the surface to be scanned. Parallel with this, further electromagnetic radiation is input into the same beam path via the dichroic deflection mirror 19', this radiation being produced by a second radiation source 27. This second radiation source 27 may be, for example, in the form of a laser diode, LED or thermal emitter. After reflection by the surface to be registered, the radiation is received again as reflected radiation RS and is guided via the scanner wheel 13 and the dichroic deflection mirror 19' back to a distance-measuring device arranged in the distance-measuring device 20. A first beam splitter 16 outputs light from the beam path onto a first spectrally selective receiver, which consists here by way of example of the combination of detector 31 and attached spectral filter 30. In an analogous manner, a second beam splitter 14' outputs light to a second spectrally selective receiver, which here likewise consists of detector 29 and attached spectral filter 28. Both spectrally selective receivers are designed so that different wavelength ranges are covered. From the ratio of the registered intensities, estimates or simple identifications of surface features can be derived. In this working example, the infrared radiation of the radiation source arranged in the distance-measuring device 20 is supplemented by the emission of a blue laser diode as second radiation source 27. The two spectrally selective receivers are designed to be sensitive in the blue and infrared range by their coordinated filters. A beam path for a camera 15 is formed axially parallel to the receiving direction of the scanning wheel 13. Alternatively, instead of two detectors with coordinated filters, it is also possible to use sensors which already have spectrally narrow-band sensitivities in the relevant range. It is also possible to use a single detector which is designed to be spectrally selective by means of different, variable filters.

Figure 11:
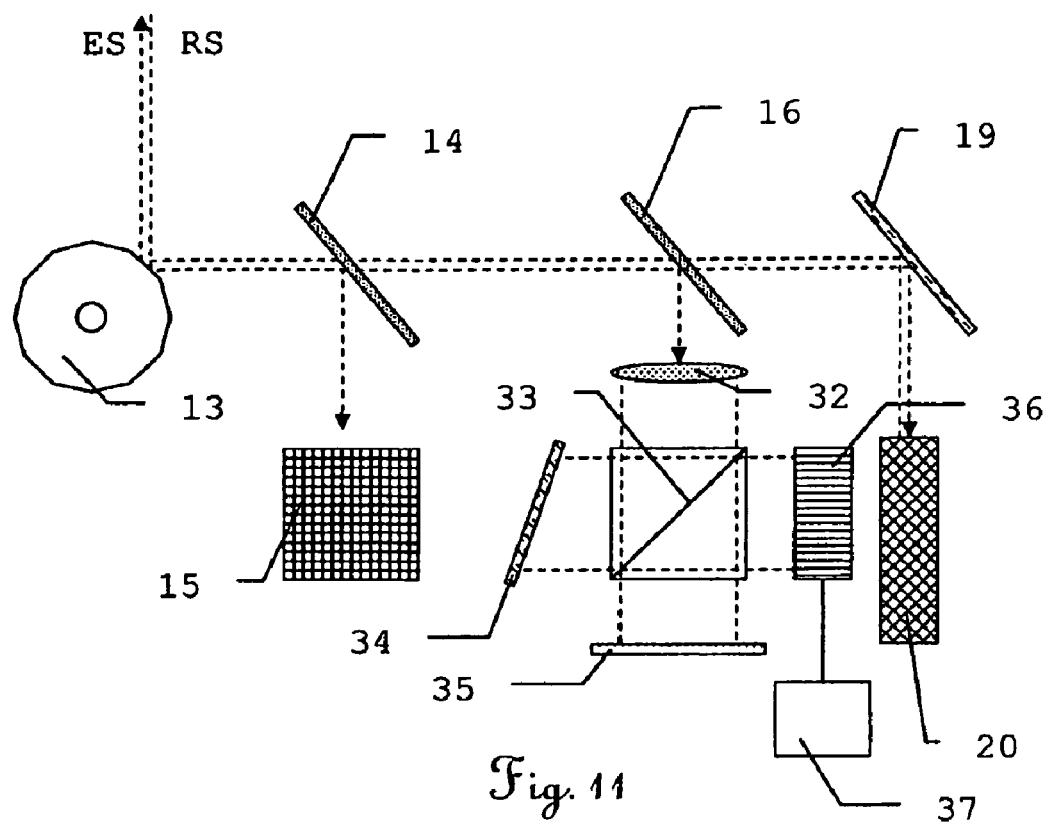
FIG. 11 shows the schematic diagram of a fourth working example of a scanner system according to the invention.

FIG. 11 shows the schematic diagram of a fourth working example of the scanner system according to the invention. A laser diode arranged in a distance-measuring device 20 emits electromagnetic radiation ES via a deflection mirror 19 and a scanner wheel 13 onto the surface to be scanned, reflected radiation RS being received via the scanner wheel 13 and the deflection mirror 19 in a distance-measuring device of the distance-measuring device 20 after reflection by the surface to be registered. A first beam splitter 16, which guides a part of the reflective radiation RS on to a Fourier spectrometer in a Michelson arrangement, is present in this beam path. Said spectrometer has a lens 32 for collimating the reflected radiation RS and a splitter plate 33 which guides the radiation on to a first interferometer mirror 35 and a tilted mirror as a second interferometer mirror 34. The radiation is guided via the splitter plate 33 with superposition onto a sensor 36, for example a linear or two-dimensional arrangement of photodiodes, the signals of which sensor are spectrally resolved in a downstream computing unit, for example by means of discrete Fourier transformation. Instead of the tilting mirror as second interferometer mirror 34, it is also possible to use a rotatable Littrow grating which can be moved by means of a piezo element or a high-precision stepper motor. This arrangement with spatial modulation permits a rapid spectral resolution which also permits operation with fast scanner movements. For the parallel image recording, a further part of the reflective radiation RS is output from the beam path via a second beam splitter 14 and is guided onto a camera 15.

Figure 12:
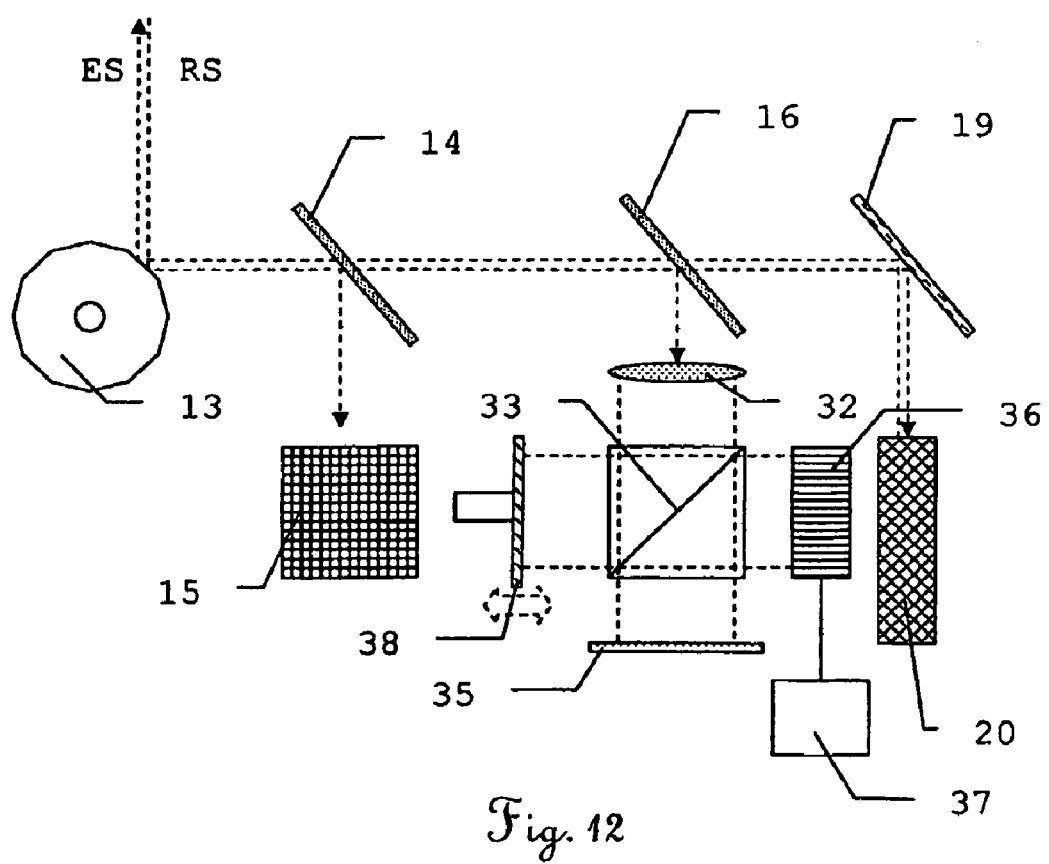
FIG. 12 shows the schematic diagram of a fifth working example of a scanner system according to the invention.

FIG. 12 shows the schematic diagram of a fifth working example which, in this example, corresponds to the working example shown in FIG. 11, except for the special type of scanning Fourier spectrometer. In this fifth working example, a Fourier spectrometer in the Michelson arrangement with a lens 32 for collimating the reflected radiation RS and a splitter plate 33 is likewise used. The radiation is guided onto a first interferometer mirror 35 and a mirror as second interferometer mirror 38, which can be moved by a piezo actuator or an electrostatic comb as a drive in the direction of one arm of the interferometer. By means of the splitter plate 33, the radiation is deflected with superposition onto a sensor 36, for example a linear or two-dimensional arrangement of photodiodes, the signals of said sensor being analyzed for spectral resolution in a downstream computing unit 37.

Figure 13:
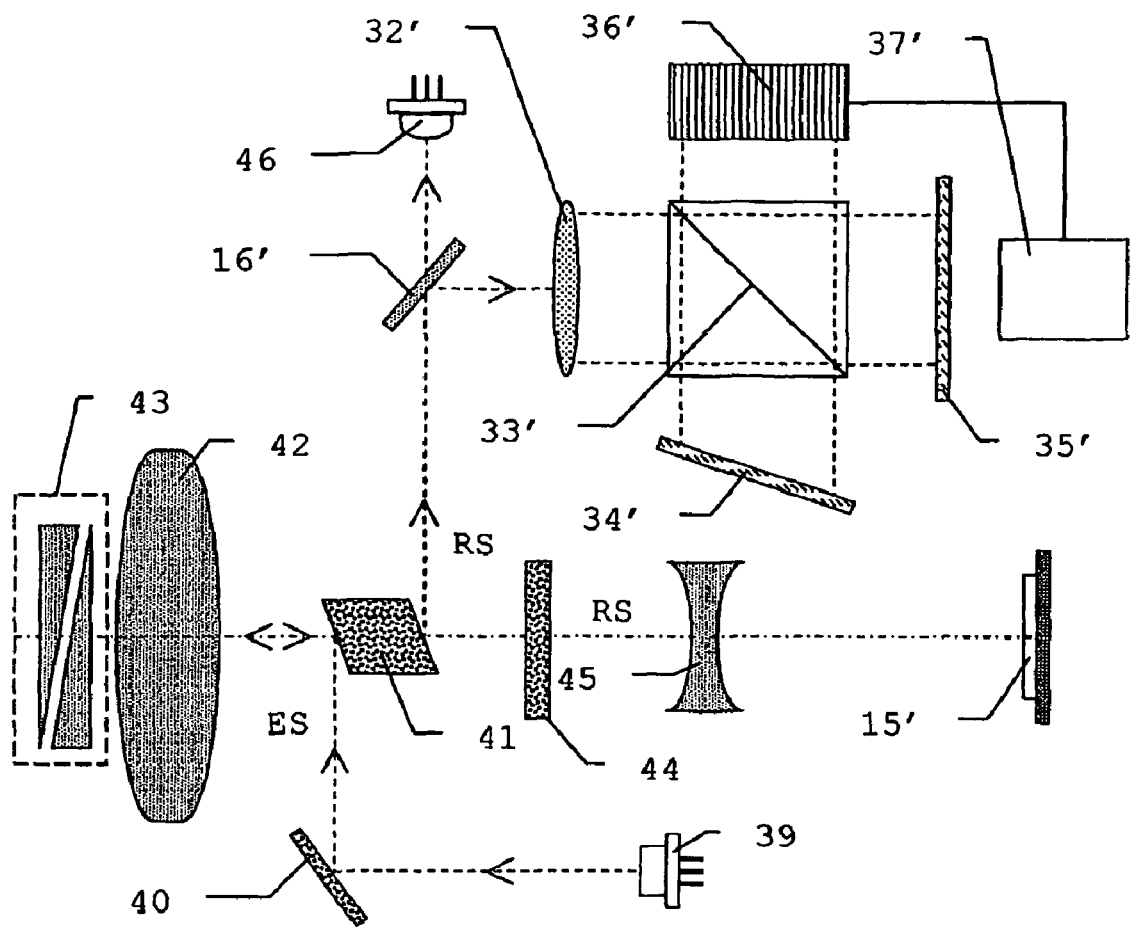
FIG. 13 shows the schematic diagram of a sixth working example of a scanner system according to the invention, with integration into a geodetic measuring device.

FIG. 13 shows the schematic diagram of a sixth working example as an example of the integration of a scanner system according to the invention into a geodetic measuring device. In a theodolite having a scanning device, a distance measurement to surface points is carried out within the field of view of the theodolite by a fixed laser diode 39 and receiving device 46. The laser diode 39 emits electromagnetic radiation ES via a deflection mirror element 40 onto a first inclined surface of a double-sided deflection mirror 41, from which this radiation is emitted via an objective lens 42 with downstream wedges 43 rotatable relative to one another as a scanning device. The radiation received again via the objective lens 42 after reflection is guided onto the second surface of the deflection mirror element 41 by a back-reflecting mirror element 44 and from there to the fixed receiving device 46. A first beam splitter 16' which outputs a part of the radiation onto a Fourier spectrometer comprising lens 32', splitter plate 33' and a first interferometer mirror 35' and a second tilted interferometer mirror 34' is present in the beam path to the receiving device 46. In a procedure analogous to the arrangement in FIG. 11, the light of the two arms of the interferometer are superposed and projected onto a sensor 36'. A downstream computing unit 37' serves for the Fourier transformation. In this working example, the scanning movement of the laserbeam for scanning a surface is effected by the wedges of the alignment means 43 which are rotatable relative to one another. The recording of an image can be effected by a camera 15' arranged in the beam path after the back-reflecting mirror element 44 and having an upstream focusing member 45.

While in FIG. 11 and FIG. 13, the—spatially variable—path difference in the Fourier spectrometer was produced by tilting of a mirror, in FIG. 12 a longitudinal movement of a mirror was effected, which movement likewise produced a path difference—now varying as a function of time. According to the invention, however, further Fourier spectrometers can also be used; thus, it is also possible to use a liquid crystal for polarization-dependent generation of an optical path difference in transmission, in particular with upstream polarization separation comprising quarter-wave plate and polarizer.

The invention claimed is:

1. A scanner system for registering and surveying surface topographies, comprising:
   one radiation source for emitting electromagnetic radiation;
   one scanning device for guiding the radiation over the surface in order to scan the surface; and
   one receiver unit for receiving the radiation reflected by the surface, the receiver unit comprising a distance-measuring device that measures distance based on a pulse transit time or phase measurement method for deriving distance information from the radiation received, wherein the radiation source and the receiver unit are formed and tuned to one another in such a way that spectral separation of the radiation takes place, such that a composition or a state of the detected surface are determinable from spectral components of the radiation.

2. A scanner system as claimed in claim 1, wherein the electromagnetic radiation includes a laser light or white light.

3. The scanner system as claimed in claim 1, wherein the radiation source emits in at least two separate wavelength ranges.

4. The scanner system as claimed in claim 1, wherein the radiation source includes:
   two laser emitters with a different wavelength; or
   one laser emitter and one terahertz emitter; or
   two spectrally broadband sources with a non-overlapping wavelength range; or
   one laser and one spectrally broadband source.

5. The scanner system as claimed in claim 1, wherein the radiation source includes a mode-coupled titanium sapphire laser with photoconductive dipole antenna.

6. A scanner system as claimed in claim 1, wherein the receiver unit has a spectrally separating sensor.

7. A scanner system as claimed in claim 6, wherein the spectrally separating sensor includes a spectrometer or a variable filter.

8. The scanner system as claimed in claim 6, wherein the receiver unit has a first beam splitter which splits the received radiation for use by the distance-measuring device and the sensor.

9. The scanner system as claimed in claim 6, wherein the spectrally separating sensor includes a prism spectrometer, a terahertz spectrometer, a grating spectrometer, or a Fourier spectrometer.

10. The scanner system as claimed in claim 9, wherein the spectrometer
   includes the Fourier spectrometer, the Fourier spectrometer is of the Michelson type and is:
   in the form of a scanning interferometer having a piezo actuator or an electrostatic comb as a drive; or
   in the form of a spatially modulating interferometer having a tilted minor or a rotatable Littrow grating.

11. The scanner system as claimed in claim 10, wherein the spatially modulating interferometer includes:
   a linear or two-dimensional photodiode array;
   a CCD camera; or
   a CMOS camera.

12. The scanner system as claimed in claim 9, wherein the Fourier spectrometer includes a liquid crystal for polarization-dependent generation of an optical path difference in transmission with upstream polarization separation, wherein the Forier spectrometer further includes a quarter-wave plate and polarizer.

13. The scanner system as claimed in claim 9, wherein the grating spectrometer is formed so as to scan as a function of time in reflection, wherein the spectrometer is formed so as to scan as a lamellar grating spectrometer or a grating on a curved and adjustable mirror.

14. The scanner system as claimed in claim 9, wherein the prism spectrometer is formed so as to scan as a function of time with a rotating prism or a rotating prism arrangement.

15. The scanner system as claimed in claim 1, further comprising a camera for image recording and/or image processing.

16. The scanner system as claimed in claim 15, further comprising a second beam splitter in the receiver unit, which guides a part of the radiation received onto the camera.

17. The scanner system as claimed in claim 1, further comprising suppression of scattered light.

18. A theodolite comprising a scanner system as claimed in claim 1.

19. A mobile scanning system for registering and/or monitoring constructions, the mobile scanning system comprising a scanner system as claimed in claim 1.

20. A method for registering surfaces by means of a scanner system, comprising the acts:
   emitting electromagnetic radiation;
   receiving radiation after reflection by the surface;
   analyzing the radiation received;
   repeating the emitting, receiving and analyzing acts several times during scanning of the surface; and
   deriving distance information based on the analysis of the radiation, wherein the analysis of the radiation is effected with spectral separation of the radiation, such that a composition or a state of the detected surface are determinable from spectral components of the radiation.

21. The method as claimed in claim 20, wherein the radiation is spectrally resolved on reception and/or the radiation is selectively emitted spectrally on emission.

22. The method as claimed in claim 20, wherein the radiation is spectrally resolved by means of interferometry on reception.

23. The method as claimed in claim 20, further comprising drawing conclusions about a chemical composition or moisture content of the surface from the spectral separation.

24. A method for registering surfaces by means of a scanner system, comprising the acts:
   emitting electromagnetic radiation;
   receiving radiation after reflection by the surface;
   analyzing the radiation received;
   repeating the emitting, receiving and analyzing acts several times during scanning of the surface; and
   deriving distance information based on the analysis of the radiation, wherein the analysis of the radiation is effected with spectral separation of the radiation; and
   determining a composition of the detected surface from spectral components of the radiation.

* * * * *

UNITED STATES PATENT AND TRADEMARK OFFICE
CERTIFICATE OF CORRECTION

PATENT NO. : 8,379,191 B2 Page 1 of 1
APPLICATION NO. : 11/610650
DATED : February 19, 2013
INVENTOR(S) : Braunecker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1756 days.

Signed and Sealed this
First Day of September, 2015

Michelle K. Lee
*Director of the United States Patent and Trademark Office*